(12) United States Patent
Franke et al.

(10) Patent No.: US 9,340,485 B2
(45) Date of Patent: May 17, 2016

(54) PROCESS FOR PREPARING ESTERS FROM FORMATES AND OLEFINICALLY UNSATURATED COMPOUNDS

(71) Applicants: Robert Franke, Marl (DE); Dieter Hess, Marl (DE); Matthias Beller, Nienhagen (DE); Ralf Jackstell, Cuxhaven Altenwalde (DE); Daniela Cozzula, Aachen (DE); Ivana Fleischer, Regensburg (DE); Reiko Jennerjahn, Sanitz (DE)

(72) Inventors: Robert Franke, Marl (DE); Dieter Hess, Marl (DE); Matthias Beller, Nienhagen (DE); Ralf Jackstell, Cuxhaven Altenwalde (DE); Daniela Cozzula, Aachen (DE); Ivana Fleischer, Regensburg (DE); Reiko Jennerjahn, Sanitz (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/366,965

(22) PCT Filed: Dec. 17, 2012

(86) PCT No.: PCT/EP2012/075766
§ 371 (c)(1),
(2) Date: Jun. 19, 2014

(87) PCT Pub. No.: WO2013/092478
PCT Pub. Date: Jun. 27, 2013

(65) Prior Publication Data
US 2014/0309435 A1    Oct. 16, 2014

(30) Foreign Application Priority Data
Dec. 19, 2011    (DE) .......... 10 2011 089 008

(51) Int. Cl.
*C07D 209/48*    (2006.01)
*C07C 69/612*    (2006.01)
*C07C 69/34*    (2006.01)
*C07C 67/38*    (2006.01)
*C07C 69/22*    (2006.01)

(52) U.S. Cl.
CPC .............. *C07C 69/22* (2013.01); *C07C 67/38* (2013.01); *C07C 69/34* (2013.01); *C07C 69/612* (2013.01); *C07D 209/48* (2013.01)

(58) Field of Classification Search
None
See application file for complete search history.

(56) References Cited

U.S. PATENT DOCUMENTS

| 7,109,346 B2 | 9/2006 | Beller et al. |
| 7,148,176 B2 | 12/2006 | Beller et al. |
| 7,495,134 B2 | 2/2009 | Hess et al. |
| 7,589,081 B2 | 9/2009 | Zapf et al. |

FOREIGN PATENT DOCUMENTS

| DE | 199 04 200 A1 | 8/2000 |
| DE | 601 03 254 T2 | 5/2005 |
| EP | 0 106 656 B1 | 9/1986 |
| JP | 59-104343 A | 6/1984 |
| JP | 2005-535695 A | 11/2005 |
| WO | WO 02/10178 A1 | 2/2002 |
| WO | WO 02/055528 A1 | 7/2002 |
| WO | WO 2004/101581 A2 | 11/2004 |
| WO | WO 2007/028660 A1 | 3/2007 |

OTHER PUBLICATIONS

International Search Report issued Feb. 28, 2013, in PCT/EP12/075766 filed Dec. 17, 2012.
Lee, et al., "Hydroesterification of Olefins Catalyzed by $Pd(OAc)_2$ Immobilized on Montmorillonite", Journal of Organic Chemistry, vol. 60, No. 1, XP055054095, Jan. 1995, pp. 250-252.
Katafuchi, et al., "Palladium-Catalyzed Hydroesterification of Alkynes Employing Aryl Formates without the Use of External Carbon Monoxide", Advanced Synthesis & Catalysis, vol. 353, No. 2-3, XP055053946, Feb. 2011, pp. 475-482.
Lin, et al., "Regiochemical Control in Palladium(0) and Palladium(II) Catalysed Alkene-Formate Ester Carbonylation Reactions", Journal of the Chemical Society, Chemical Communications, No. 4, XP055053947, Jan. 1989, pp. 248-249.
Search Report issued Aug. 29, 2012 in European Patent Application No. 10 2011 089 088.4 (with English translation of category of cited documents).

*Primary Examiner* — Kamal Saeed
(74) *Attorney, Agent, or Firm* — Oblon, McClelland, Maier & Neustadt, L.L.P.

(57) ABSTRACT

The invention provides a process for preparing esters from formates and olefinically unsaturated compounds with catalysts based on palladium compounds. In addition, the invention discloses a polyphasic reaction mixture and nonyl methyl ester mixtures prepared by the process according to the invention.

12 Claims, 1 Drawing Sheet

PROCESS FOR PREPARING ESTERS FROM FORMATES AND OLEFINICALLY UNSATURATED COMPOUNDS

The present invention relates to a method of producing esters from formates and olefinically unsaturated compounds by carbonylation with catalysts based on palladium-containing compounds. The invention further discloses a multiphasic reaction mixture and also nonoic acid methyl ester mixtures obtained by the method of the present invention.

RELATED ART

Figure 1:
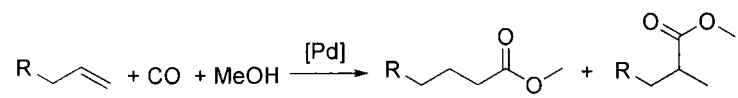

Esters, especially esters bearing linear moieties of preferably 8, 9 and 10 carbon atoms, are industrially important for use as plasticizers. Linear and branched esters are also produced for a multiplicity of applications as specialty and fine chemicals such as drugs, scents and insecticides. The esterification of carboxylic acids and the direct methoxycarbonylation of olefins in the presence of carbon monoxide and a palladium catalyst are the most important methods used in industry for production of linear esters (see FIG. 1).

The methodology of carbonylating with formates is reviewed in Appl. Catal. A 1995 p. 25-44. Altogether, esters are manufactured by carbonylation at a rate of more than 120 000 metric tons a year.

In the literature, there are very few research results in the carbonylation with formates. The catalysts generally used in this context contain ruthenium, iridium or palladium in the presence of various additives, such as promoters, ligands or acids. Ethylene is used as the sole olefin source in almost all the reactions which are known. As the number of carbon atoms in the olefin increases, all processes suffer an enormous reduction in activity, accompanied by enormous losses in chemoselectivity. Since the systems which are known for carbonylation with formates are mostly ligand-free systems, poor regioselectivities are obtained here with higher olefins as well as poor activity and chemoselectivity.

The analogous production of esters from carbon monoxide and methanol is a thoroughly investigated process. Its disadvantages are the need to use costly high-pressure apparatus and the use of pure carbon monoxide, which is quite costly and highly toxic and is produced from fossil resources.

In summary, no hydroesterification process is known for reacting higher olefins than ethylene as well as ethylene, especially olefin-containing mixtures, with good chemoselectivities (>95%), good regioselectivities (>90%), good activities (TOF>100 $h^{-1}$) and—when olefin-containing mixtures comprising internal carbon-carbon double bonds are used—under isomerizing conditions while not using carbon monoxide as a reactant. It is necessary to hit these numbers if industrial conversions are to be achieved.

PURPOSE OF THE INVENTION

For the abovementioned reasons there is an immense need for novel improved methods of carbonylating olefinically unsaturated compounds, especially olefin-containing mixtures comprising internal as well as other carbon-carbon double bonds, with formates. A particular purpose is to make even long-chain olefins having more than 2 carbon atoms accessible to carbonylation with formates, i.e. without use of carbon monoxide as a reactant. An accompanying objective is the achievement of high n-selectivities, i.e. the formation of n-terminal esters even from olefin-containing mixtures, and of such activity levels as are required for industrial application.

SUMMARY OF THE INVENTION

In contrast to the thoroughly investigated production of esters from carbon monoxide and methanol, the method presented herein requires only one substrate, and that is in the liquid state. This substrate, the formate, is an adduct formed from carbon monoxide and an alcohol. It is obtainable from the hydrogenation of $CO_2$ and thus involves a chemical process which helps to reduce greenhouse gases. The production of esters from carbon monoxide and methanol, by contrast, gets its carbon monoxide raw material mainly from fossil resources, such as coal gasification.

DETAILED DESCRIPTION OF THE INVENTION

The invention provides a method of producing esters by carbonylation, characterized in that it is carried out
i) using at least one palladium-containing compound,
ii) at least one olefinically unsaturated compound,
iii) at least one phosphorus-containing ligand,
iv) at least one formate,
v) at least one alcohol,
vi) at least one acid,
vii) in a temperature range of 80° C. to 120° C.,
viii) at a reaction pressure of 0.1 to 0.6 MPa.

The palladium-containing catalyst comprises a phosphorus-containing ligand and an acid in a palladium:ligand ratio ranging from 1:1.1 to 1:100 and a palladium:acid ratio ranging from 1:1 to 1:1000 and all ratios are molar ratios.

The target reaction has a preference for temperatures of 60 to 180° C., more preferably 80 to 120° C.

The method of the present invention may also utilize solvents for the catalyst. The solvents used are generally polar inert organic solvents, water or the alcohol corresponding to the particular formate, for example methanol in the case of methyl formate and ethanol in the case of ethyl formate. Examples include dipolar aprotic solvents, aliphatic ethers, amides, aromatic compounds, alcohols and esters and also mixtures thereof. The alcohols corresponding to the particular formate are particularly preferable.

Useful sources of palladium include any palladium-containing salts and complexes in the form of a precursor which form palladium-hydride complexes under the reaction conditions. Examples include Pd(II) halides (e.g. $Pd(II)Cl_2$), Pd(II) complexes (e.g. Pd(II) acetylacetonate, Pd(II) acetate, Pd(II) dibenzylideneacetone), Pd(0) complexes (e.g. $Pd(0)[PPh_3]_4$). The palladium compounds can be in different oxidation states from 0 to +II which react with the acid and the formate to form the corresponding active palladium-hydride complexes.

Palladium acetylacetonate is a particularly preferred precursor.

To achieve the desired catalytic selectivities and catalytic activities, a phosphorus-containing ligand has to be added. The present method employs this ligand in excess relative to the palladium. The palladium-to-ligand ratio is preferably between 1:2 to 1:50.

Useful ligands include any desired ligands comprising trivalent phosphorus and capable of forming a coordinative bond with the central palladium atom. A suitable example is α,α'-bis(di-t-butylphosphino)-o-xylene, represented by formula 1 and hereinbelow abbreviated as BuPoX. The binding of ligands can be not only monodentate but also multidentate. Bidentate ligands are preferred.

A particularly preferred ligand is α,α'-bis(di-t-butylphosphino)-o-xylene, represented by formula 1:

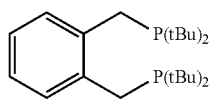

Useful acids include strong acids of pKa below 4, preferably sulphonic acids. Particular preference is given to methanesulphonic acid and p-toluenesulphonic acid from the group of sulphonic acids.

Olefins are unsaturated compounds capable of being selectively reacted using the catalyst systems mentioned. Terminal alkenes and aromatic olefins having between 2 and 20 carbon atoms, and mixtures thereof, are particularly preferred. Olefins of 6 to 12 carbon atoms and mixtures thereof are particularly preferred. Branched and internal olefins can likewise be reacted.

The method of the present invention will prove particularly advantageous for the production of esters having 3 to 21 carbon atoms. The production of esters having 7 to 13 carbon atoms is preferred in particular.

The olefins may be in a functionalized state and include not only carbon and hydrogen but also further, hetero atoms, for example nitrogen and/or oxygen. Without claim to completeness, unsaturated alcohols, ethers, amines, esters, carboxylic acids, amides, urethanes, halides, aldehydes, ketones and epoxides may be mentioned here as useful substrates.

The invention further provides a multiphasic reaction mixture containing at least one olefinically unsaturated compound and at least one ester formed by the method of the present invention.

The method of the present invention achieves turnover number values [(TON)=product (mol)/palladium (mol)] for the catalysts on the order of 3400 or more in batch operation. Therefore, between 0.038 mol % of palladium (based on olefin substrate) is typically used.

Because the catalyst activities are good, the method of the present invention can use very small amounts of catalyst.

The method of the present invention is particularly surprising and novel in that no comparatively long-chain and highly stereo- and regioselective esters of olefins with sufficient activity have been described in the past. The method described herein shows for the first time that good yields and n-selectivities of n-terminal esters are possible under the conditions of the present invention. The particular advantages of the novel method are that no gases, especially no carbon monoxide, are any longer needed as a reactant, to perform a carbonylation.

It is additionally possible to produce the formates from the greenhouse gas $CO_2$. This enables esters to be produced using an environmentally friendly and less complex process.

Catalyst activities likewise have to be high for industrial use. The method of the present invention provides them. 1-Octene for instance at a turnover frequency or reaction rate constant of above 209 $h^{-1}$ and a turnover number of 3400 in batch operation. The result was accordingly a space-time yield of 16.2 g/(l*h) or 0.016 t/($m^3$*h).

The esters obtained according to the present invention are useful inter alia as intermediates for plasticizer alcohols and for pharmaceuticals and agrochemicals and also as building blocks for polymers.

EXAMPLES

The examples which follow illustrate the method of the present invention.

General protocol for production of esters from formate and olefinically unsaturated compounds using a palladium/phosphine/acid catalyst:

A 100 ml stainless steel autoclave is charged with 54.5 mmol of 1-octene (8.5 ml), Pd(acac)$_2$, 0.038 mol % (6.3 mg), 0.13 mol % of BuPoX (28.4 mg), 10 ml of methyl formate, 10 ml of methanol and 20 µl of methanesulphonic acid under a protective gas (argon or nitrogen for example). The autoclave is heated to 100° C. to establish a final pressure of 0.51 MPa, followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography.

General information see note [a] in Table 1.

Table 1 hereinbelow shows changes of some reaction parameters, for example the variation of ligands having the following structures:

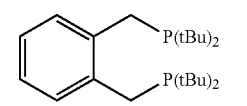

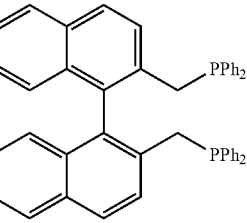

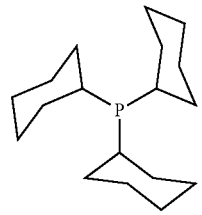

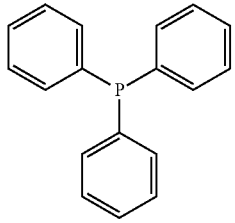

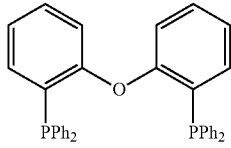

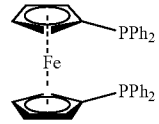

The possible product spectrum which the method of the present invention provides on using 1-octene and methyl formate is apparent from reaction (1):

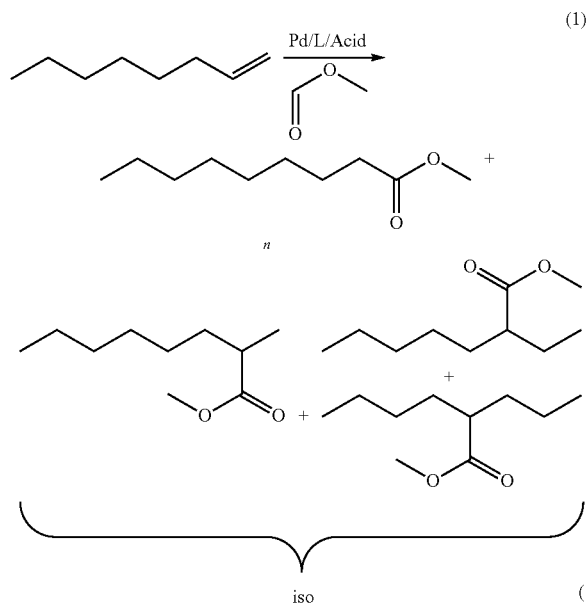

The invention further provides a nonoic acid methyl ester mixture obtained by the method of the present invention.

TABLE 1

Palladium-catalysed methoxycarbonylation of 1-octene.

| Example | Ligand | Acid | T [° C.] | MeOH/MF [ml/ml] | Yield [%][b] | n-Sel. [%] |
|---|---|---|---|---|---|---|
| 1 | 1 | MeSO₃H | 100 | 10/10 | 46[c] | 95 |
| 2 | 1 | pTsOH | 100 | 10/10 | 36[c] | 95 |
| 3 | 1 | HOAc | 100 | 10/10 | 0 | — |
| 4 | 1 | — | 100 | 10/10 | 0 | — |
| 5 | 1 | MeSO₃H | 80 | 10/10 | 34 | 95 |
| 6 | 1 | MeSO₃H | 100 | 10/10 | 98 | 94 |
| 7 | 1 | MeSO₃H | 120 | 10/10 | 79 | 93 |
| 8 | 1 | MeSO₃H | 100 | 0/10 | 28 | 95 |
| 9 | 1 | MeSO₃H | 100 | 10/10 | 98 | 94 |
| 10 | 2 | MeSO₃H | 100 | 10/10 | 0 | — |
| 11 | 3 | MeSO₃H | 100 | 10/10 | 0 | — |
| 12 | 4 | MeSO₃H | 100 | 10/10 | 0 | — |
| 13 | 5 | MeSO₃H | 100 | 10/10 | 0 | — |
| 14 | 6 | MeSO₃H | 100 | 10/10 | 0 | — |

[a] unless otherwise stated, the reactions were carried out at 100° C. with 0.038 mol %, of Pd(acac)₂, L/Pd=4 (L=BuPoX=1), 10 ml of methylformate, 10 ml of methanol, acid/L=4 (=20 μl MeSO₃H), 54 mmol of olefin. [b] determined by gas chromatography using an internal standard. [c] yields following a reaction time of 5.5 h.

Example 1

A 100 ml stainless steel autoclave is charged with 54.5 mmol of 1-octene (8.5 ml), Pd(acac)₂, 0.038 mol % (6.3 mg), 0.13 mol % of BuPoX (28.4 mg), 10 ml of methyl formate, 10 ml of methanol and 20 μl of methanesulphonic acid under a protective gas (argon or nitrogen for example). The autoclave is heated to 100° C. to establish a final pressure of 5.1 bar, followed by stirring at that temperature for 5.5 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. methyl nonanoate, is 43.7%. The yield of branched products (methyl 2-methyloctanoate, methyl 2-ethylheptanoate and methyl 2-propylhexanoate) is altogether 2.3%. The total yield of methyl esters is accordingly 46% with an n:iso ratio of 95:5.

Example 2

A 100 ml stainless steel autoclave is charged with 54.5 mmol of 1-octene (8.5 ml), Pd(acac)₂, 0.038 mol % (6.3 mg), 0.13 mol % of BuPoX (28.4 mg), 10 ml of methyl formate, 10 ml of methanol and 58 mg of p-toluenesulphonic acid under a protective gas (argon or nitrogen for example). The autoclave is heated to 100° C. to establish a final pressure of 5.1 bar, followed by stirring at that temperature for 5.5 h. The autoclave is subsequently cooled down to room temperature and the residual pressure is released. A 5 ml quantity of isooctane is added to the reaction solution as an internal standard and the mixture is analysed by gas chromatography. The yield of branched products (methyl 2-methyloctanoate, methyl 2-ethylheptanoate and methyl 2-propylhexanoate) is altogether 1.8%. The total yield of methyl esters is accordingly 36% with an n:iso ratio of 95:5.

Example 3

A 100 ml stainless steel autoclave is charged with 54.5 mmol of 1-octene (8.5 ml), Pd(acac)₂, 0.038 mol % (6.3 mg), 0.13 mol % of BuPoX (28.4 mg), 10 ml of methyl formate, 10 ml of methanol and 17.6 μl of acetic acid under a protective gas (argon or nitrogen for example). The autoclave is heated to 100° C. to establish a final pressure of 5.1 bar, followed by stirring at that temperature for 5.5 h. The autoclave is subsequently cooled down to room temperature and the residual pressure is released. A 5 ml quantity of isooctane is added to the reaction solution as an internal standard and the mixture is analysed by gas chromatography. The yield of methyl nonanoate is 0%.

Example 4

A 100 ml stainless steel autoclave is charged with 54.5 mmol of 1-octene (8.5 ml), Pd(acac)₂, 0.038 mol % (6.3 mg), 0.13 mol % of BuPoX (28.4 mg), 10 ml of methyl formate, 10 ml of methanol and no acid under a protective gas (argon or nitrogen for example). The autoclave is heated to 100° C. to establish a final pressure of 5.1 bar, followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of methyl nonanoate is 0%.

Example 5

A 100 ml stainless steel autoclave is charged with 54.5 mmol of 1-octene (8.5 ml), Pd(acac)₂, 0.038 mol % (6.3 mg), 0.13 mol % of BuPoX (28.4 mg), 10 ml of methyl formate, 10 ml of methanol and 20 μl of methanesulphonic acid under a protective gas (argon or nitrogen for example). The autoclave is heated to 80° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. methyl nonanoate, is 32.3%. The yield of branched products (methyl 2-methyloctanoate, methyl 2-ethylheptanoate and methyl 2-propylhexanoate) is altogether 1.7%. The total yield of methyl esters is accordingly 34% with an n:iso ratio of 95:5.

Example 6

A 100 ml stainless steel autoclave is charged with 54.5 mmol of 1-octene (8.5 ml), Pd(acac)$_2$, 0.038 mol % (6.3 mg), 0.13 mol % of BuPoX (28.4 mg), 10 ml of methyl formate, 10 ml of methanol and 20 μl of methanesulphonic acid under a protective gas (argon or nitrogen for example). The autoclave is heated to 100° C. to establish a final pressure of 5.1 bar, followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. methyl nonanoate, is 92.1%. The yield of branched products (methyl 2-methyloctanoate, methyl 2-ethylheptanoate and methyl 2-propylhexanoate) is altogether 5.9%. The total yield of methyl esters is accordingly 98% with an n:iso ratio of 94:6.

Example 7

A 100 ml stainless steel autoclave is charged with 54.5 mmol of 1-octene (8.5 ml), Pd(acac)$_2$, 0.038 mol % (6.3 mg), 0.13 mol % of BuPoX (28.4 mg), 10 ml of methyl formate, 10 ml of methanol and 20 μl of methanesulphonic acid under a protective gas (argon or nitrogen for example). The autoclave is heated to 120° C. to establish a final pressure of 5.1 bar, followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. methyl nonanoate, is 73.5%. The yield of branched products (methyl 2-methyloctanoate, methyl 2-ethylheptanoate and methyl 2-propylhexanoate) is altogether 5.5%. The total yield of methyl esters is accordingly 79% with an n:iso ratio of 93:7.

Example 8

A 100 ml stainless steel autoclave is charged with 54.5 mmol of 1-octene (8.5 ml), Pd(acac)$_2$, 0.038 mol % (6.3 mg), 0.13 mol % of BuPoX (28.4 mg), 10 ml of methyl formate and 20 μl of methanesulphonic acid under a protective gas (argon or nitrogen for example). The autoclave is heated to 100° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of methyl nonanoate is 28% with an n:iso ratio of 95:5.

Example 9 corresponds to Example 6

Examples 10-14

A 100 ml stainless steel autoclave is charged with 54.5 mmol of 1-octene (8.5 ml), Pd(acac)$_2$, 0.038 mol % (6.3 mg), ligand (Example 10: 55 mg of ligand 2; Example 11: 116 mg of ligand 3; Example 12: 163 mg of ligand 4; Example 13: 44.6 mg of ligand 5; Example 14: 39.2 mg of ligand 6), 10 ml of methyl formate, 10 ml of methanol and 20 μl of methanesulphonic acid under a protective gas (argon or nitrogen for example). The autoclave is heated to 100° C. to establish a final pressure of 5.1 bar, followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of methyl nonanoate is 0% in all cases.

Since olefin mixtures are frequently used in the industry, one core competency of an industrially useful catalyst is good isomerization of olefins coupled with highly selective n-terminal functionalization.

Figure 2:
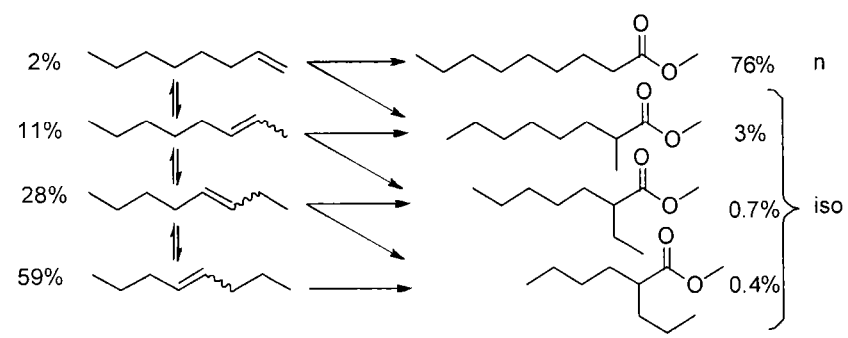

One particular embodiment of the invention utilizes an olefin-containing mixture comprising internal carbon-carbon double bonds as olefinically unsaturated compound. The performance capability of the proposed system is demonstrated on such a technical-grade mixture in FIG. 2; see also Example 16.

The invention further provides a nonoic acid methyl ester mixture obtained by the method of the present invention.

Reaction (2) indicates the general course.

The substituents R$_1$, R$_2$ and R$_3$ correspond to the groups or portions of the compounds shown in the "Olefin" and "Product" columns of Examples 15 to 23 hereinbelow.

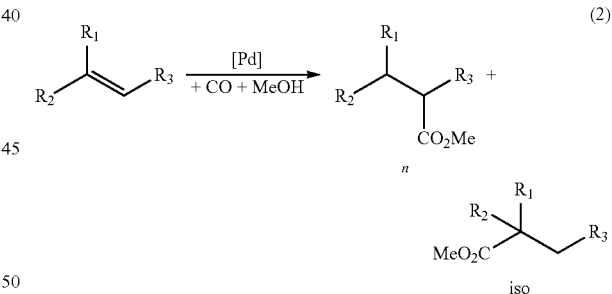

The examples in Table 2 show the unsaturated starting compounds (olefin and formate) and the products obtained. The n-selectivity column indicates the proportions of product having an n-terminal ester group.

TABLE 2

| Example | Olefin | Formate ester | Yield [%][b] | n-Selectivity | Product |
|---|---|---|---|---|---|
| 15 | ~~~~= | O‖O⁀ | 98 | 94 | ~~~~~⁀O⁀ |

TABLE 2-continued

| Example | Olefin | Formate ester | Yield [%][b] | n-Selectivity | Product |
|---|---|---|---|---|---|
| 16 | 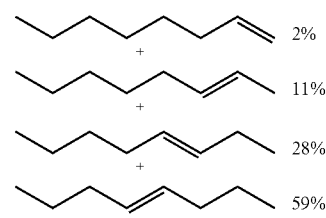 2% +  11% + 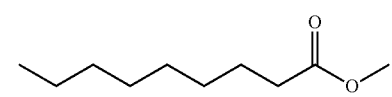 28% + 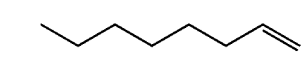 59% |  | 80 | 94 | 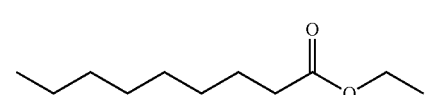 |
| 17 | 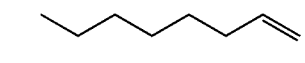 |  | 99 | 95 | 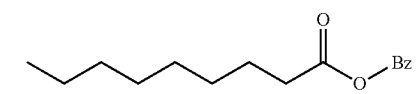 |
| 18 | 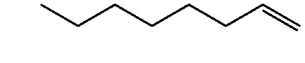 | 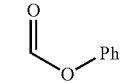 | 86 | 92 | 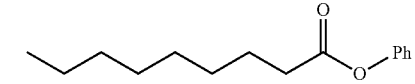 [SMILES: CCCCCCCCC(=O)Oc1ccccc1] |
| 19 | 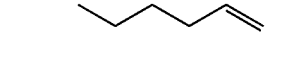 |  | 46 | 93 | 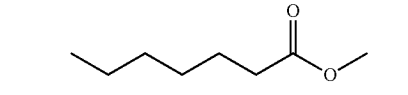 |
| 20 | 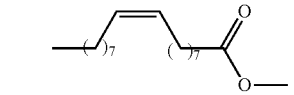 |  | 86 | 95 | 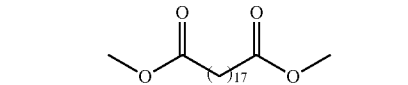 |
| 21[e] | 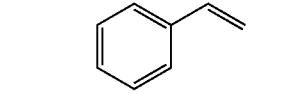 |  | 82 | 88 | 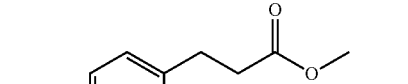 |
| 22[c] | 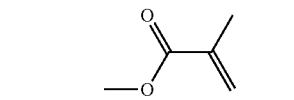 |  | 98 | 89 | 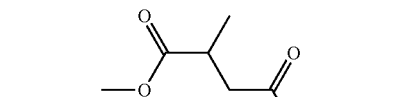 |
| 23[c] | 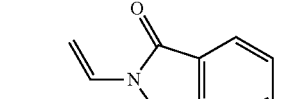 |  | 81 | >99 | 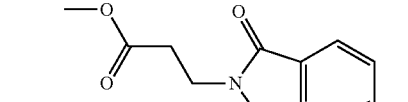 |
| 24[c] | | | 56 | >99 | |

[a]reactions were at 100° C. with 6.3 mg (0.038 mol % when using 54 mmol of olefin) of Pd(acac)$_2$, L/Pd = 4 (L = BuPoX), 10 ml of formate, 10 ml of alcohol (alcohol corresponding to formate used), acid/L = 4 (=20 µl of MeSO$_3$H), 54 mmol of olefin.
[b]determined by gas chromatography using an internal standard.
[c]27 mmol of olefin.
[d]formate screening conditions.
[e]10 mmol of methyl oleates, 0.3 mol % of Pd(acac)$_2$, reaction tim 166 h.

Example 15 corresponds to Example 6

Example 16

A 100 ml stainless steel autoclave is charged with 54.5 mmol of octene mixture (8.5 ml consisting of: 2% of 1-octene, 11% of 2-octene, 28% of 3-octene, 59% of 4-octene), Pd(acac)$_2$, 0.038 mol % (6.3 mg), 0.13 mol % of BuPoX (28.4 mg), 10 ml of methyl formate, 10 ml of methanol and 20 μl of methanesulphonic acid under a protective gas (argon or nitrogen for example). The autoclave is heated to 100° C. to establish a final pressure of 5.1 bar, followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. methyl nonanoate, is 75.2%. The yield of branched products (methyl 2-methyloctanoate, methyl 2-ethylheptanoate and methyl 2-propylhexanoate) is altogether 4.8%. The total yield of methyl esters is accordingly 80% with an n:iso ratio of 94:6.

Example 17

A 100 ml stainless steel autoclave is charged with 19.3 mmol of 1-octene (3 ml), Pd(acac)$_2$, 0.16 mol % (9.4 mg), 124 μmol of BuPoX (49 mg), 10 ml of ethyl formate, 10 ml of ethanol and 28 μl of methanesulphonic acid under a protective gas (argon or nitrogen for example). The autoclave is heated to 120° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. ethyl nonanoate, is 94.1%. The yield of branched products (ethyl 2-methyloctanoate, ethyl 2-ethylheptanoate and ethyl 2-propylhexanoate) is altogether 4.9%. The total yield of ethyl esters is accordingly 99% with an n:iso ratio of 95:5.

Example 18

A 100 ml stainless steel autoclave is charged with 19.3 mmol of 1-octene (3 ml), Pd(acac)$_2$, 0.16 mol % (9.4 mg), 124 μmol of BuPoX (49 mg), 10 ml of benzyl formate, 10 ml of benzyl alcohol and 28 μl of methanesulphonic acid under a protective gas (argon or nitrogen for example). The autoclave is heated to 120° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of branched products (benzyl 2-methyloctanoate, benzyl 2-ethylheptanoate and benzyl 2-propylhexanoate) is altogether 6.9%. The total yield of benzyl esters is accordingly 86% with an n:iso ratio of 92:8.

Example 19

A 100 ml stainless steel autoclave is charged with 19.3 mmol of 1-octene (3 ml), Pd(acac)$_2$, 0.16 mol % (9.4 mg), 124 μmol of BuPoX (49 mg), 10 ml of phenyl formate, 10 ml of phenol and 28 μl of methanesulphonic acid under a protective gas (argon or nitrogen for example). The autoclave is heated to 90° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. phenyl nonanoate, is 42.8%. The yield of branched products (phenyl 2-methyloctanoate, phenyl 2-ethylheptanoate and phenyl 2-propylhexanoate) is altogether 3.2%. The total yield of phenyl esters is accordingly 46% with an n:iso ratio of 93:7.

Example 20

A 100 ml stainless steel autoclave is charged with 54.8 mmol of 1-hexene (6.8 ml), Pd(acac)$_2$, 0.038 mol % (6.3 mg), 0.13 mol % of BuPoX (28.4 mg), 10 ml of methyl formate, 10 ml of methanol and 20 μl of methanesulphonic acid under a protective gas (argon or nitrogen for example). The autoclave is heated to 100° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. methyl heptanoate, is 81.7%. The yield of branched products (methyl 2-methylhexanoate and methyl 2-ethylpentanoate) is altogether 4.3%. The total yield of methyl esters is accordingly 86% with an n:iso ratio of 95:5.

Example 21

A 100 ml stainless steel autoclave is charged with 10 mmol of methyl oleate (3.4 ml), 9.4 mg of Pd(acac)$_2$, 124 μmol of BuPoX (49 mg), 10 ml of methyl formate, 10 ml of methanol and 26 μl of methanesulphonic acid under a protective gas (argon or nitrogen for example). The autoclave is heated to 100° C., followed by stirring at that temperature for 166 h. The autoclave is subsequently cooled down to room temperature and the residual pressure is released. The product has precipitated as a solid. A 5 ml quantity of isooctane is added to the reaction solution as an internal standard and methanol is added until all of it has dissolved. The mixture is then analysed by gas chromatography. The yield of n-product, i.e. dimethyl eicosanedioate, is 72.2%. The yield of branched products (for example dimethyl 2-methylnonadecanedioate, dimethyl 2-ethyloctadecanedioate) is altogether 9.8%. The total yield of methyl esters is accordingly 82% with an n:iso ratio of 88:12.

Example 22

A 100 ml stainless steel autoclave is charged with 27 mmol of styrene (3.1 ml), Pd(acac)$_2$, 0.08 mol % (6.3 mg), 28.4 mg of BuPoX, 10 ml of methyl formate, 10 ml of methanol and 20 μl of methanesulphonic acid under a protective gas (argon or nitrogen for example). The autoclave is heated to 100° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. methyl 3-phenylpropionoate, is 87.2%. The yield of the branched product methyl 2-phenylpropionate is 10.8%. The total yield of methyl esters is accordingly 98% with an n:iso ratio of 89:11.

Example 23

A 100 ml stainless steel autoclave is charged with 27.2 mmol of methyl methacrylate (2.9 ml), Pd(acac)$_2$, 0.08 mol % (6.3 mg), 28.4 mg of BuPoX, 10 ml of methyl formate, 10 ml of methanol and 20 μl of methanesulphonic acid under a protective gas (argon or nitrogen for example). The autoclave is heated to 100° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. dimethyl 2-methylsuccinate, is 81%. Branched products were not detectable. The total yield of methyl esters is accordingly 81% with an n:iso ratio of 100:0.

Example 24

A 100 ml stainless steel autoclave is charged with 27 mmol of N-vinylphthalimide, Pd(acac)$_2$, 0.08 mol % (6.3 mg), 28.4 mg of BuPoX, 10 ml of methyl formate, 10 ml of methanol and 20 μl of methanesulphonic acid under a protective gas (argon or nitrogen for example). The autoclave is heated to 100° C., followed by stirring at that temperature for 20 h. The autoclave is subsequently cooled down to room temperature and the residual pressure is released. A 5 ml quantity of isooctane is added to the reaction solution as an internal standard and the mixture is analysed by gas chromatography. The yield of n-product, i.e. the methyl ester of N-phthaloyl-β-alanine, is 56%. Branched products were not detectable. The total yield of methyl esters is accordingly 56% with an n:iso ratio of 100:0.

The very good yields and selectivities of the method according to the present invention are clear from the examples.

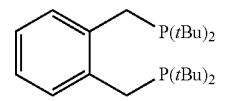

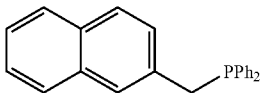

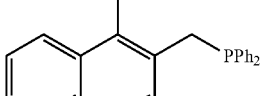

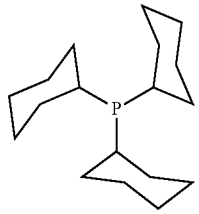

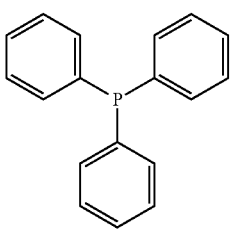

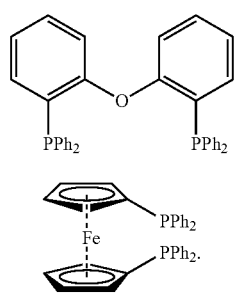

The invention claimed is:

1. A method of producing esters by carbonylation, wherein the method is carried out:
   i) with at least one palladium-containing compound;
   ii) at least one olefinically unsaturated compound selected from the group consisting of unsaturated olefins having between 2 and 20 carbon atoms, unsaturated alcohols, unsaturated ethers, unsaturated amines, unsaturated esters, unsaturated carboxylic acids, unsaturated amides, unsaturated urethanes, unsaturated halides, unsaturated aldehydes, unsaturated ketones, and unsaturated epoxides;
   iii) at least one phosphorus-containing compound comprising a trivalent phosphorous;
   iv) at least one formate;
   v) at least one alcohol;
   vi) at least one acid;
   vii) in a temperature range of 80° C. to 120° C.; and
   viii) at a reaction pressure of 0.1 to 0.6 MPa.

2. The method of claim 1, wherein the phosphorus-containing compound has a bidentate structure.

3. The method of claim 2, wherein the phosphorus-containing compound having a bidentate structure has formula 1:

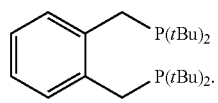

4. The method of to claim 1, wherein the formate is selected from methyl formate, ethyl formate, benzyl formate, phenyl formate.

5. The method of claim 4, wherein the at least one alcohol corresponds to the particular formate used.

6. The method of claim 1, wherein the acid is selected from the group of sulphonic acids.

7. The method of claim 6, wherein the sulphonic acids are selected from methanesulphonic acid, p-toluenesulphonic acid.

8. The method of claim 1, that wherein the at least one olefinically unsaturated compound is an olefin-containing mixture comprising unsaturated olefin compounds having 6 to 12 carbon atoms.

9. The method of to claim 8, wherein the carbonylation is effected with isomerization to the n-terminal ester.

10. The method of claim 1, wherein the olefinically unsaturated compounds comprise nitrogen and/or oxygen and is selected from the group consisting of unsaturated alcohols, unsaturated ethers, unsaturated amines, unsaturated esters, unsaturated carboxylic acids, unsaturated amides, unsaturated urethanes, unsaturated halides, unsaturated aldehydes, unsaturated ketones, and unsaturated epoxides.

11. The method of claim 1, wherein the palladium-containing compound with palladium in the oxidation states 0 to +II is selected from the group consisting of:
   palladium halides;
   palladium acetylacetonate;
   palladium acetate;
   palladium dibenzylideneacetone; and
   palladium triphenylphosphine.

12. The method of claim 1, wherein the phosphorus-containing compound is selected from the group consisting of phosphorous-containing compounds of formula (1), (2), (3), (4), (5), and (6):